(12) United States Patent
DeBeliso et al.

(10) Patent No.: US 7,631,557 B2
(45) Date of Patent: Dec. 15, 2009

(54) GRIP FORCE TRANSDUCER AND GRIP FORCE ASSESSMENT SYSTEM AND METHOD

(76) Inventors: Mark DeBeliso, 4235 S. Rimview Way, Boise, ID (US) 83716; John W. McChesney, 1856 N. Estancia Pl., Eagle, ID (US) 83616; Louis E. Murdock, 4504 W. Quail Ridge Dr., Boise, ID (US) 83703

(*) Notice: Subject to any disclaimer, the term of this patent is extended or adjusted under 35 U.S.C. 154(b) by 22 days.

(21) Appl. No.: 12/019,520

(22) Filed: Jan. 24, 2008

(65) Prior Publication Data

US 2009/0025475 A1   Jan. 29, 2009

Related U.S. Application Data

(60) Provisional application No. 60/886,380, filed on Jan. 24, 2007.

(51) Int. Cl.
*A61B 1/24* (2006.01)
(52) U.S. Cl. .................................. 73/379.02
(58) Field of Classification Search .............. 73/370.02, 73/760–860, 379.01–379.09
See application file for complete search history.

(56) References Cited

U.S. PATENT DOCUMENTS

| | | | |
|---|---|---|---|
| 4,939,933 A | 7/1990 | Curran | |
| 4,949,729 A | 8/1990 | Haski | |
| 4,970,819 A | 11/1990 | Mayhak | |
| 5,010,772 A | 4/1991 | Bourland et al. | |
| 5,157,970 A | 10/1992 | Lewis, Jr. | |
| 5,316,479 A | 5/1994 | Wong et al. | |
| 5,429,140 A | 7/1995 | Burdea et al. | |
| 5,447,167 A | 9/1995 | Fleischaker | |
| 5,467,656 A * | 11/1995 | Teare et al. | 73/862.541 |
| 5,511,571 A * | 4/1996 | Adrezin et al. | 135/66 |
| 5,662,123 A | 9/1997 | Goldman | |
| 5,681,993 A * | 10/1997 | Heitman | 73/379.02 |
| 5,833,634 A | 11/1998 | Laird et al. | |
| 5,911,693 A | 6/1999 | Prochazka et al. | |
| 5,916,180 A | 6/1999 | Cundari et al. | |
| 5,983,727 A | 11/1999 | Wellman et al. | |

(Continued)

OTHER PUBLICATIONS

Interactive Motion Technologies, Inc.; website; printed Dec. 21, 2006; 4 pages; http://interactive-motion.com/html/hardware.htm.

(Continued)

*Primary Examiner*—Max Noori
(74) *Attorney, Agent, or Firm*—Holland Law Office PLLC

(57) ABSTRACT

A grip force assessment device, method and system that can provide a grip force map image presenting a detailed image of the complex grip capability/capacity of a human hand including the palm and all digits improving over existing assessment systems and their attendant inaccuracy, poor reliability, and lack of meaningful clinical relevance. The grip force assessment system includes a grip force transducer including a high-resolution tactile array that produces a high-resolution grip force signal. A processing device processes, analyzes and outputs grip force data. A display provides a grip force map image showing distribution of individual finger function relative to entire hand function. The grip force transducer includes a high-resolution tactile sensor wherein the greatest distance between adjacent pressure sensing nodes is in the range of 1.0 mm to 10.0 mm.

8 Claims, 6 Drawing Sheets

U.S. PATENT DOCUMENTS

| | | | |
|---|---|---|---|
| 5,989,199 A | 11/1999 | Cundari et al. | |
| 6,033,370 A | 3/2000 | Reinbold et al. | |
| 6,063,031 A | 5/2000 | Cundari et al. | |
| 6,091,981 A | 7/2000 | Cundari et al. | |
| 6,179,790 B1 | 1/2001 | Cundari et al. | |
| 6,231,525 B1 | 5/2001 | Paske | |
| 6,264,621 B1 | 7/2001 | Paske | |
| 6,276,471 B1 * | 8/2001 | Kratzenberg et al. | 180/19.3 |
| 6,500,119 B1 | 12/2002 | West et al. | |
| 6,595,933 B2 | 7/2003 | Sarvazyan et al. | |
| 6,606,907 B1 | 8/2003 | Rosendahl | |
| 6,716,034 B2 | 4/2004 | Casanova, Jr. et al. | |
| 6,725,728 B1 | 4/2004 | Lee | |
| 6,763,126 B2 | 7/2004 | Recce | |
| 6,817,130 B2 | 11/2004 | Ivanov | |
| 7,096,731 B1 | 8/2006 | Lee | |
| 7,409,765 B2 * | 8/2008 | So | 30/123 |
| 2004/0031180 A1 | 2/2004 | Ivanov | |
| 2005/0192676 A1 | 9/2005 | Sears et al. | |
| 2006/0063647 A1 | 3/2006 | Jones-Glaser | |
| 2006/0260417 A1 | 11/2006 | Son et al. | |

OTHER PUBLICATIONS

Tekscan, Inc.; entitled Medical Pressure Measurement Overview; printed Dec. 22, 2006; 2 pages; http://www.tekscan.com/medical.html.

Pressure Profile Systems Inc.; entitled TactArray; printed Dec. 27, 2006; 1 page; http://www.pressureprofile.com/tactarray.php.

Pressure Profile Systems Inc.; entitled Conformable Tactile Array; printed Dec. 27, 2006; 1 page; http://www.pressureprofile.com/tactarraytype.php?type=conformable.

Pressure Profile Systems Inc.; entitled IMT Gets a Grip on Grasp Force with PPS; printed Dec. 27, 2006; 2 pages; http://www.pressureprofile.com/casestudy.php?c5=4.

Tekscan, Inc.; entitled Tekscan Technology; printed Jan. 15, 2008; 4 pages; http://www.tekscan.com/technology.html.

Sensor Products Inc.; entitled Tactile Surface Pressure Mapping—About Us; printed Jan. 15, 2008; 3 pages; http://www.sensorprod.com/aboutus.php.

Pressure Profile Systems Inc.; entitled Capacitive Sensing; printed Jan. 15, 2008; 3 pages; http://www.pressureprofile.com/technology-capacitive.php.

NK Biotechnical Corporation; entitled the NK Digit-Grip Device; printed Jan. 09, 2008; 12 pages; http://www.nkb.com/motor.htm.

* cited by examiner

GRIP FORCE TRANSDUCER AND GRIP FORCE ASSESSMENT SYSTEM AND METHOD

RELATED APPLICATIONS

This application claims the priority of Provisional Application Ser. No. 60/886,380 Grip Force Transducer and Mapping System, filed Jan. 24, 2006, the content of said application being incorporated herein by reference.

BACKGROUND OF THE INVENTION

1. Field of the Invention

This invention relates generally to devices and methods for measuring physical performance and more particularly to a device that assesses the complex grip capability/capacity of a human hand.

2. Background

Strength testing of the injured hand and forearm is of immense interest to injured patients, treating physicians, therapists, and insurance providers. The Jamar Hand Dynamometer, (herein "the Jamar"), has been the standard clinical strength-testing device of injured and diseased hands for over 40 years.

The Jamar is used to measure grip force by means of grasping two offset parallel bars that can be situated at one of five preset positions to accommodate various hand sizes. The subject is asked to squeeze the offset parallel bars of the device and the highest force exerted is measured and displayed on a mechanical gage. The Jamar is essentially isometric in use and allows almost no perceptible motion of the handles. The Jamar has survived in the face of criticism for inaccuracy, questionable reliability, and lack of meaningful clinical relevance. The handles of the Jamar are parallel offset bars that represent a very limited number of tasks found in activities of daily living. The Jamar is of little use when evaluating the function of a finger or fingers and offers little meaningful information regarding grip analysis. It is believed by some that the Jamar survives because of cost, ease of use, availability, and lack of a suitable replacement.

Medical examinations performed by physicians and therapists rely upon the Jamar to evaluate the functional capacity and disability of the hand, evaluations which directly affect employment and injury award compensation. In addition to the aforementioned limitations, the Jamar is vulnerable to fraudulent efforts on behalf of the subject. Malingering manipulation and falsification at the will of the examinee are an ever-present concern with significant financial ramifications. Patient effort is best surmised through a series of testing methods that distract the subject during testing, however the results of such methods are suspected to yield unacceptable levels of false positives.

Alternative hand strength testing devices have been designed, tested, and marketed but have failed to gain acceptance. Such testing devices based upon pneumatic and spring mechanisms have been trialed, but have been criticized for inaccuracy, poor reliability, and lack of meaningful clinical relevance. In addition, like the Jamar, specific analysis about individual finger function in the context of the function of entire hand cannot be acquired. Finally, like the Jamar, insight into patient effort can be only surmised through a series of testing methods, which distract the subject during testing. Because these devices were found to be no better and in some manners worse than the Jamar, broad acceptance for implementation of non-hydraulic dynamometers has failed to occur.

Accordingly, there is a need for an improved grip assessment tool that can measure the complex grip capability/capacity of a human hand without the constraints and design drawbacks observed in the prior art. Additionally, advantage may be found in providing a device, method and system for the assessment of grip force that provides analysis and output relating to individual finger function in the context of the function of entire hand.

Therefore one object of the present invention is to provide a device, method and system for the assessment of grip force that provides analysis and output including a display of grip force data representative of individual finger function in the context of the function of entire hand. A further objective of the present invention is to provide a device, method and system for the assessment of grip force that can collect, condition, analyze and output data and imagery representative of a complex grip capability/capacity of a human hand including the palm and all digits. Yet another objective of the present invention is to provide a device, method and system for the assessment of grip force that can provide a grip force map image that presents a detailed rendering of the complex grip capability/capacity of a human hand including the palm and all digits that will provide an improvement over existing assessment systems and their attendant inaccuracy, poor reliability, and lack of meaningful clinical relevance.

SUMMARY OF THE INVENTION

The present invention relates to a grip force transducer and system and method for the assessment of grip force. A grip force transducer is connected to a processing device. The processing device is adapted to process output from the grip force transducer and provide:

a) analysis of data representative of individual finger function relative to entire hand function, b) real time graphic feedback and imagery depicting function of an individual finger, and/or the complex grip capability/capacity of the hand, c) two and/or three dimensional imagery and mapping including time lapse imagery and mapping of the grip surface depicting force distribution, d) representation of the grip surface depicting relative forces across a color spectrum, or a gray scale spectrum with an increase in force being represented by color values reaching one or the other ends of the visible spectrum, e) an ability to manipulate a grip force map image by magnification, rotation, variation of image resolution, variation of force scales and variation of image color, f) representation of the grip surface depicting relative forces as a relative increase or decrease in landscape peaks and valleys, g) a record of grip force distribution over time, h) hard-copy reports for documentation.

The present invention is directed to a grip force transducer including a bounded three dimensional geometric transducer body defined by an outer surface. The grip force transducer includes a high-resolution tactile array that provides a high-resolution grip force signal representative of a grip force being applied at any given time at any of a plurality of nodes of the high-resolution tactile array.

Tactile array sensing involves the measurement of tactile force or pressure. A high-resolution tactile sensor includes an array of electrodes that measure the distribution of tactile pressure over a surface. A typical fabric based tactile sensor array includes a first plurality of parallel electrodes that are placed over a second plurality of electrodes with a non-conductive elastic isolation layer positioned between the first and second pluralities of parallel electrodes. The plurality of electrodes can be made of a stretchable material with each electrode formed as one or more metallic or metallized strands. A capacitor is formed at each of the intersections of the first and second pluralities of parallel electrodes define individual pressure sensing nodes. The pressure sensing nodes are selectively scanned and a capacitance at that node and therefore the pressure or force exerted at the node may be measured.

The term high-resolution tactile sensor as used herein means an array having a density of pressure sensing nodes wherein the greatest distance between adjacent pressure sensing nodes is 10.0 mm, and preferably the distance between adjacent pressure sensing nodes in the range of 1.0 mm to 10.0 mm.

A bounded three dimensional geometric transducer body may include cylindrical, ovidal, frustoconical, spherical, elliptical as well as other regularly and irregularly and undulate shaped bodies. These bodies may emulate or include commonly gripped surfaces to reflect tasks encountered during activities of daily living and/or may impose hand grip position to facilitate specific muscular strength assessment. For instance in one embodiment, a cylindrical grip force transducer may have a radius of approximately 50 mm, and a length of approximately 150 mm. In another embodiment, a cylindrical grip force transducer may have a radius of approximately 25 mm, and a length of approximately 150 mm. In yet another embodiment, a spherical grip force transducer may have a radius of approximately 25 mm-50 mm. In yet another embodiment, a frustoconical grip force transducer may have a primary radius of approximately 31.75 mm, a secondary radius of approximately 12 mm, and a length of approximately 200 mm. Furthermore, a transducer may be of a freeform shape including undulating surfaces to accommodate individual digits. The grip force transducers are designed in a number of different sizes that allow for the assessment of grip by individuals with small to very large hands. The grip force measured while grasping the grip sensor transducer permits clear assessment of the functional capability/capacity of the finger(s), the palm and the phalange(s).

Grip force transducers may be interchangeable, depending on a specific testing goal, patient hand size or task that for which emulation is desired. Connection between the grip force transducer and the processing device may be by cable or wireless connection. The shapes and sizes of the grip force transducers were selected to assess hand function in a manner that mimics, but is not limited to, activities of daily living. Signal from the grip sensor transducer is relayed to a laptop computer wirelessly or via a connection cable and a signal processor. Software generates graphic and quantitative force map presentation of the data.

The grip force assessment system includes hardware and software required to amplify, modulate, multiplex and digitize the output from the grip force transducer as required. A processing device is adapted to process the conditioned output from the grip force transducer, analyzing grip force data and providing an output representative of grip force capacity that may be displayed or sent to an imaging device. The grip force system is adapted to display an output representative of a grip force generated between the hand, fingers and the grip force transducer. Alternately grip at the finger tips or between the thumb and a single digit may be assessed. In a preferred embodiment, the output representative of a grip force is presented as a grip force map or graph that allows real time visual correlation between the display and grip function.

The grip force assessment system of the present invention is capable of assessing a complex grip capability/capacity of the human hand by mapping contact force distribution generated while grasping the grip force transducer. Repeatability of measurements is assured by calibration of the high-resolution tactile array. As a result, it would be difficult for malingering manipulation to occur. It would be highly unlikely that an individual could exert the precise motor control over the entire surface of the hand required to generate a false positive given the reliability, high resolution, and variable shapes of the grip force transducers.

The primary applications of the grip force assessment system and method are, but are not limited to, medical evaluation of hand function, and ergonomic solutions related to the design of safe and efficient hand-implement couplings for sport and work place implements, as tools and sports equipment.

The foregoing has outlined rather broadly the features and technical advantages of the present invention so that the detailed description of the invention that follows may be better understood. Additional features and advantages of the invention will be described hereinafter, which form the subject of the invention. It should be appreciated by those skilled in the art that the conception and the specific embodiments disclosed might be readily used as a basis for modifying or designing other grip assessment devices for carrying out the same purposes of the present invention. It should also be realized by those skilled in the art that such equivalent constructions do not depart from the spirit and scope of the invention as set forth herein.

BRIEF DESCRIPTION OF THE DRAWINGS

The accompanying drawings, which are incorporated in and form a part of the specification, illustrate the embodiments of the present invention, and, together with the description, serve to explain the principles of the invention. In the drawings.

It is to be noted that the drawings illustrate only typical embodiments of the invention and are therefore not to be considered limiting of its scope, for the invention will admit to other equally effective embodiments.

DETAILED DESCRIPTION

Figure 1:
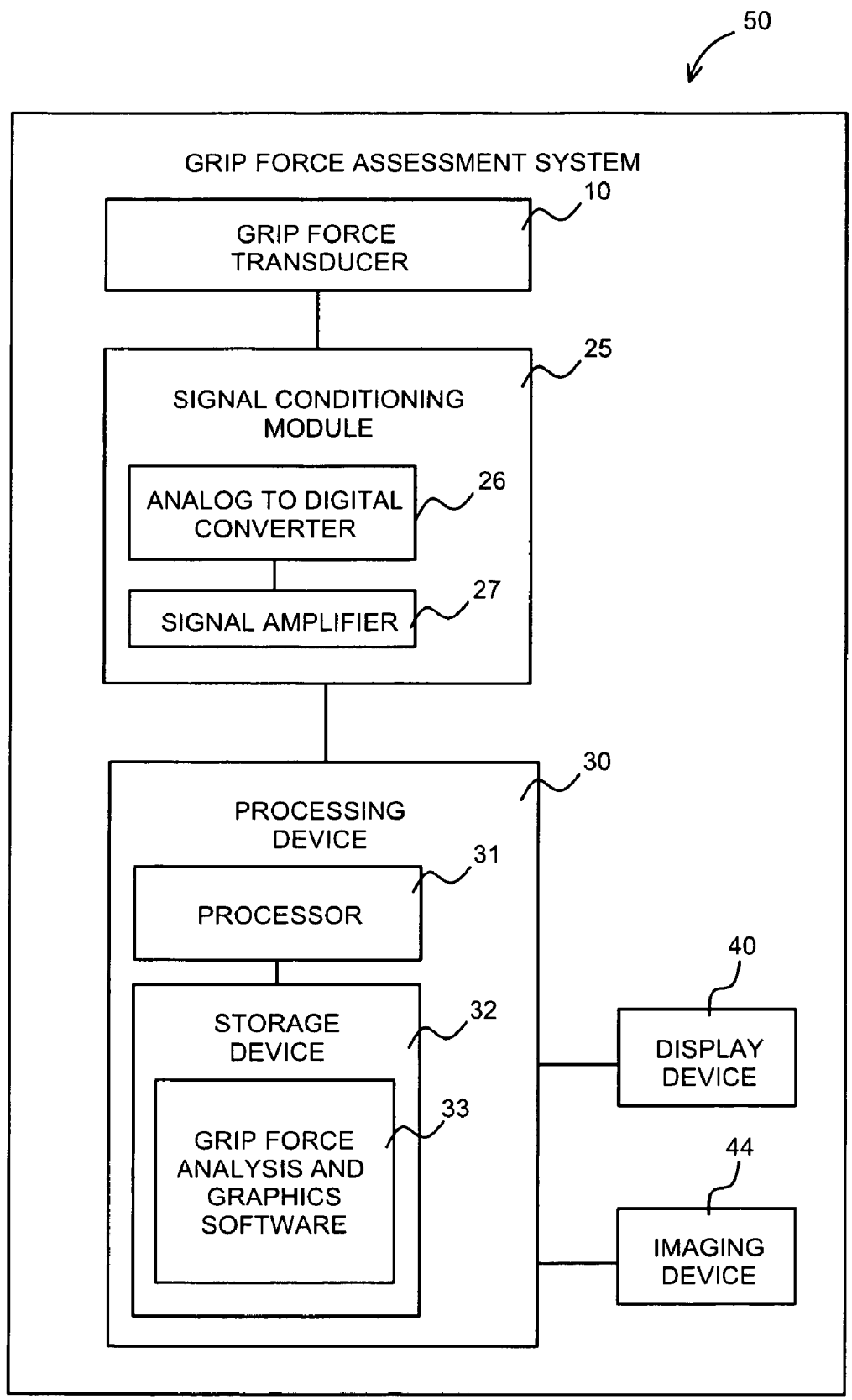
FIG. 1 is a schematic representation of a grip force assessment system according to the present invention.

Referring to FIG. 1, grip force assessment system 50 includes grip force transducer 10 connected to processing device 30, for instance a common laptop computer or other processing device capable of supporting the functions of grip force assessment system 50. Processing device 30 includes processor 31 and storage device 32 for storing electronic files including data and executable programs such as grip force analysis and graphics software 33. Signal conditioning module 25 is connected between processor 30 and grip force transducer 10. Signal processing module 25 includes analog to digital converter 26 for converting an analog signal of grip force transducer 10 to a digital signal for processing and/or storage. Signal processing module 25 also includes signal amplification 27. As shown, processed grip force data can be output by a variety of known means including display device 40 and imaging device 44.

Figure 2:
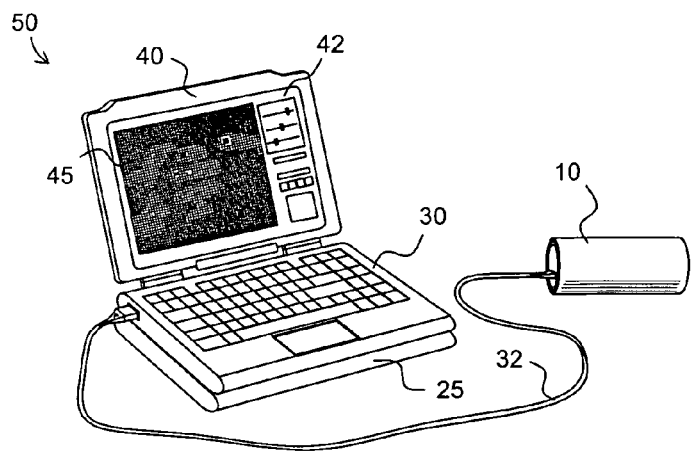
FIG. 2 is a representation of a grip force assessment system according to the present invention.

FIG. 2 graphically depicts grip force assessment system 50 including grip force transducer 10 connected to processing device 30, in this case a laptop computer. Processing device 30. Signal conditioning module 25 is connected to processor 30. Cable 32 connects grip force transducer 10 to signal conditioning module 25. Display device 40, in this instance the LCD video display of the laptop computer, displays grip force screen display 42 showing grip force map image 45.

Figure 3:
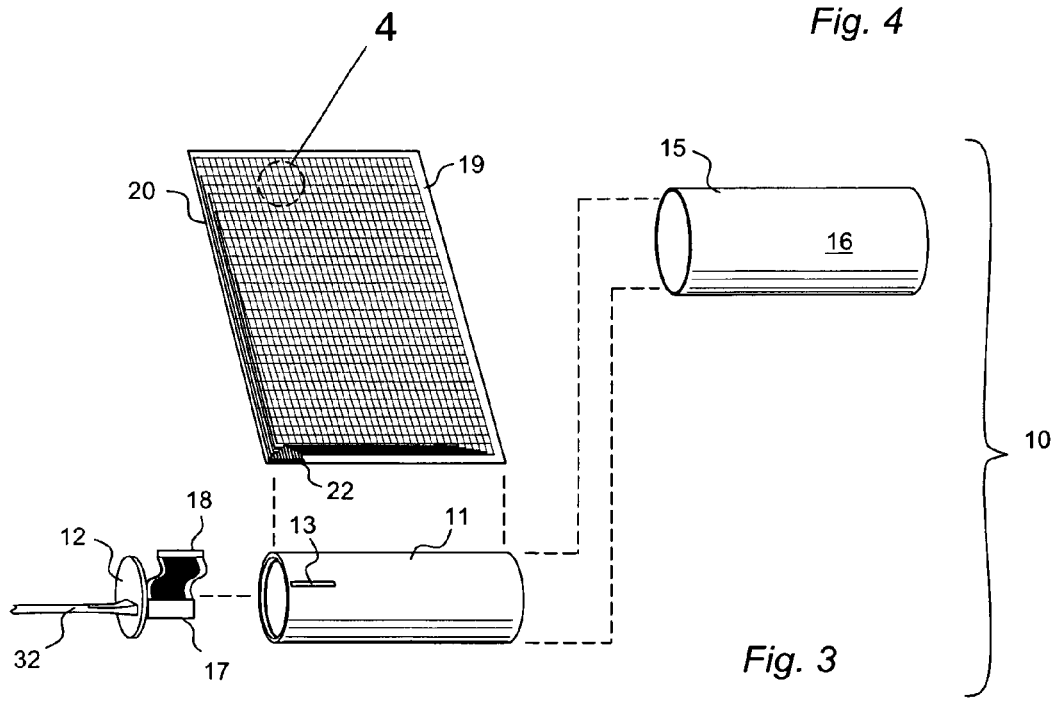
FIG. 3 is an exploded perspective representation of a grip force transducer according to the present invention.

FIG. 3 is an exploded perspective representation of grip force transducer 10 showing transducer body 11 about which high-resolution tactile array 20 is wrapped. Neoprene sleeve 15 is positioned about high-resolution tactile array 20 and an outer surface of neoprene sleeve 15 forms gripping surface 16 of grip force transducer 10.

Figure 4:
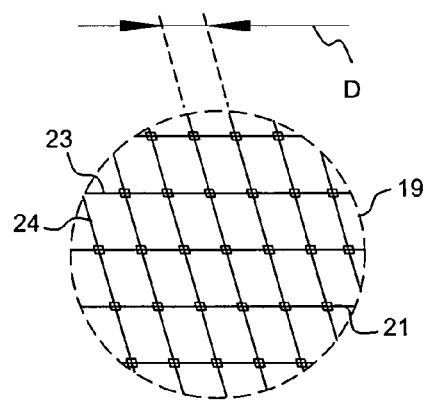
FIG. 4 is a representative detail of a high-resolution tactile array according to the present invention.

Referring to FIG. 4, high-resolution tactile array 20 is formed as a dielectric matrix including a fabric substrate 19. A first plurality of electrodes 23 are arranged in a grid against second plurality of electrodes 24 forming a plurality of nodes 21. In the preferred embodiment, a distance D between adjacent pressure sensing nodes 21 is in the range of 1.0 mm to 10.0 mm. In one embodiment of the invention, high-resolution tactile array 20 for a typical hand held transducer would include in the range of one thousand nodes 21. Each of the first plurality of electrodes 23 and the second plurality of electrodes 24 terminate at conductive strip 22. End piece 12 fits into the open end of transducer body 11 and cable 32, attaches to conductor strip 17 and connector 18 which is conductively connected to conductive strip 22 through aperture 13 formed in transducer body 11.

Figure 5:
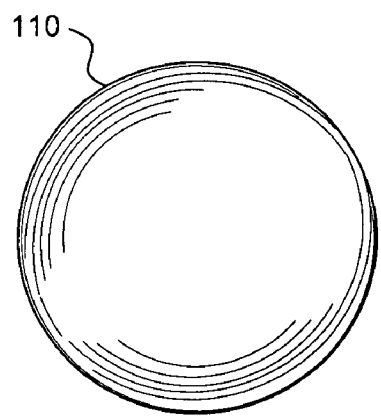
FIG. 5 illustrates an alternate shape of a grip force transducer according to the present invention.
Figure 6:
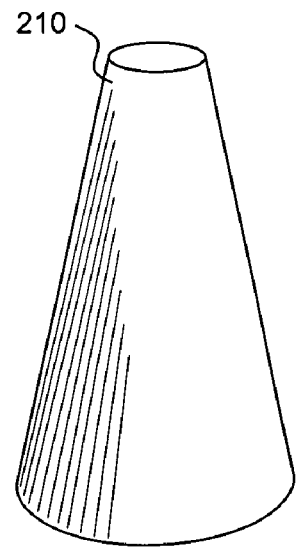
FIG. 6 illustrates an alternate shape of a grip force transducer according to the present invention.
Figure 7:
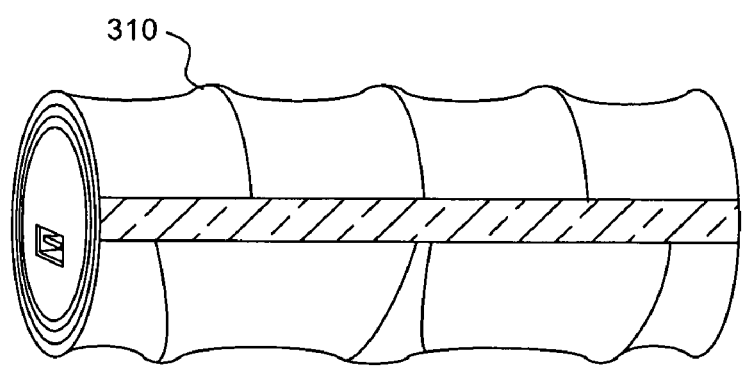
FIG. 7 illustrates an alternate shape of the grip force transducer according to the present invention.

FIGS. 5-7 illustrate alternate shape shapes for grip force transducers 110, 210 and 310 respectively.

Figure 8:
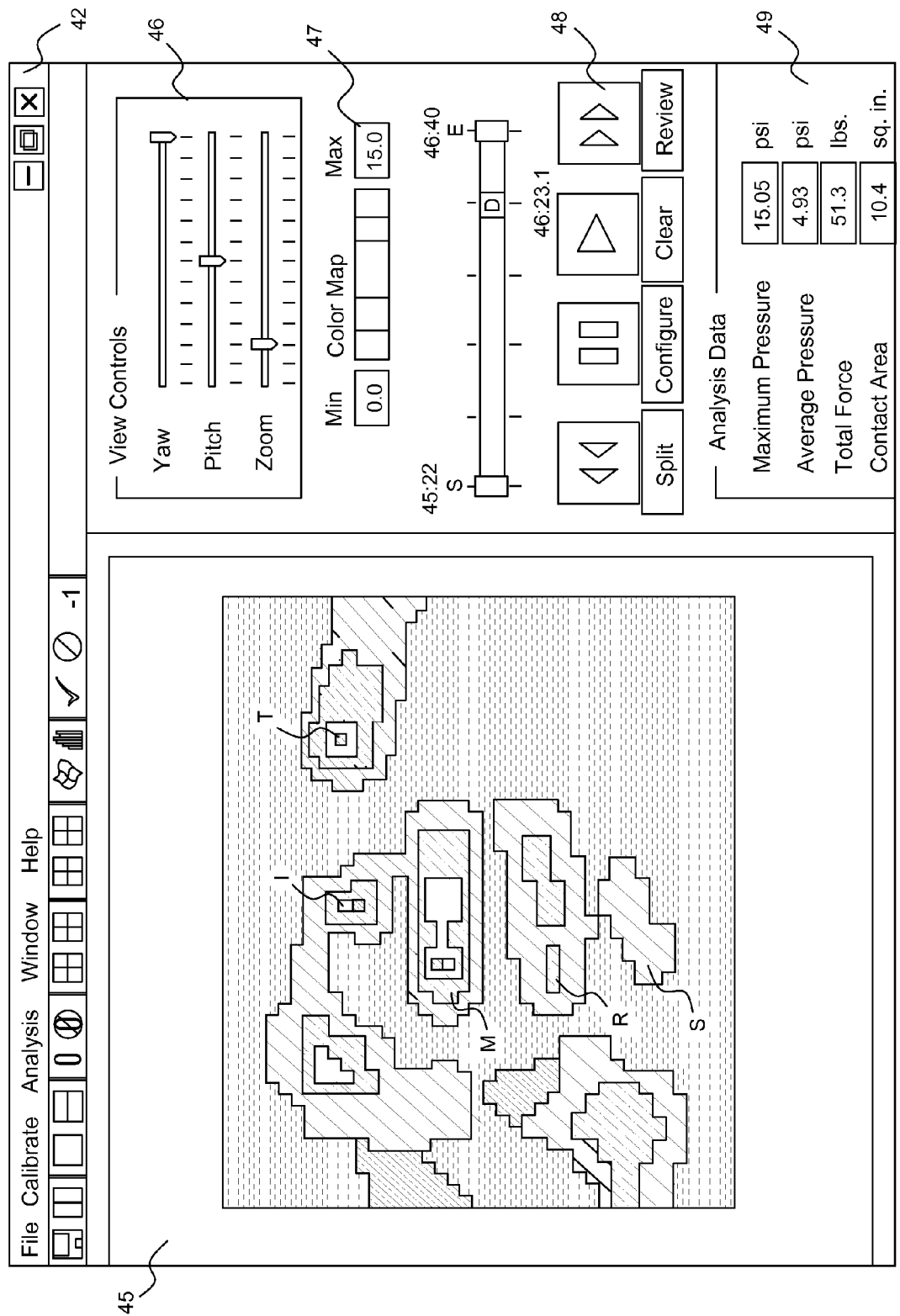
FIG. 8 illustrates a grip force screen display including a two dimensional grip force map image according to the present invention.

FIG. 8 illustrates grip force screen display 42 which shows grip force map image 45, a two dimensional representation of grip force applied against a grip force transducer. Grip force map image 45 shows the various digits of a hand, thumb T, index finger I, middle finger M, ring finger R and small finger S. In addition, grip force map image 45 shows the relative differences in grip force observed at any interpolated point of the hand, as represented in grip force map image 45. This feature is achieved by depicting various force values i.e. kilograms/cm$^2$, newtons/m$^2$), pounds per square inch or the like, as colors on a visual spectrum or shades of a grey scale.

Figure 9:
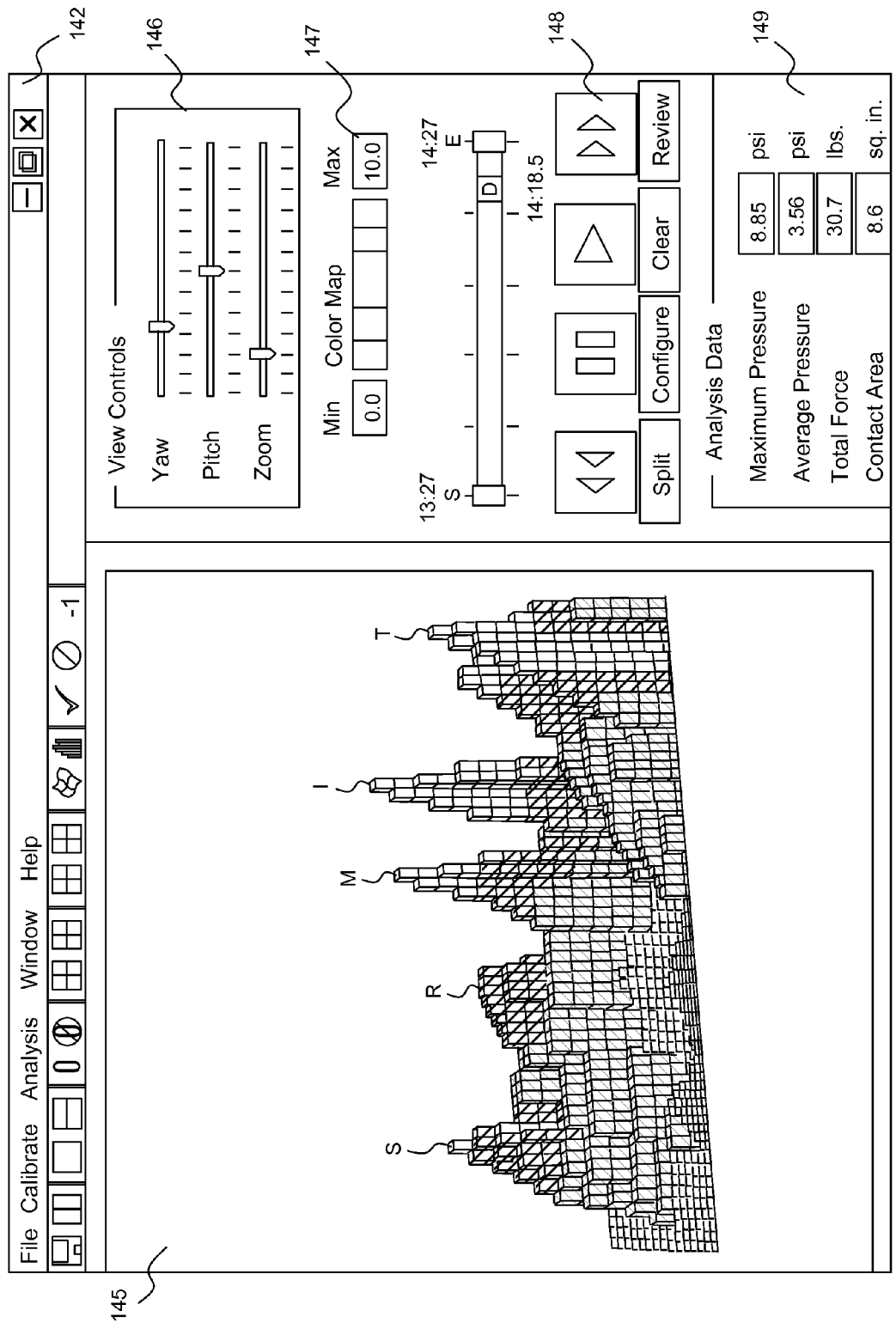
FIG. 9 illustrates a grip force screen display including a three dimensional grip force map image according to the present invention.

FIG. 9 illustrates grip force screen display 142 which shows grip force map image 145, a three dimensional representation of grip force applied against a grip force transducer. Grip force map image 145 shows the various digits of a hand, thumb T, index finger I, middle finger M, ring finger R and small finger S. In addition, grip force map image 145 shows the relative differences in grip force observed at any point on the hand, as represented in grip force map image 145. This feature is achieved by depicting various force values i.e. kilograms/cm$^2$, newtons/m$^2$), pounds per square inch or the like, as colors on a visual spectrum or shades of a grey scale together with a varying height scale, the combination of which provide a visual landscape depicting peaks of a defined color or range of the visual spectrum to valleys of a defined color or range of the visual spectrum.

As shown in FIG. 8, grip force screen display 42 provides graphic user interface for a number of functions including view control 46, color control 47, animation play controls 48 and data analysis display 49. Similarly, as seen in FIG. 9, grip force screen display 142 provides graphic user interface for functions including view control 146, color control 147, animation play controls 148 and data analysis display 149. Other graphic functions are enabled as well in the preferred embodiment including resolution enhancement.

Figure 10:
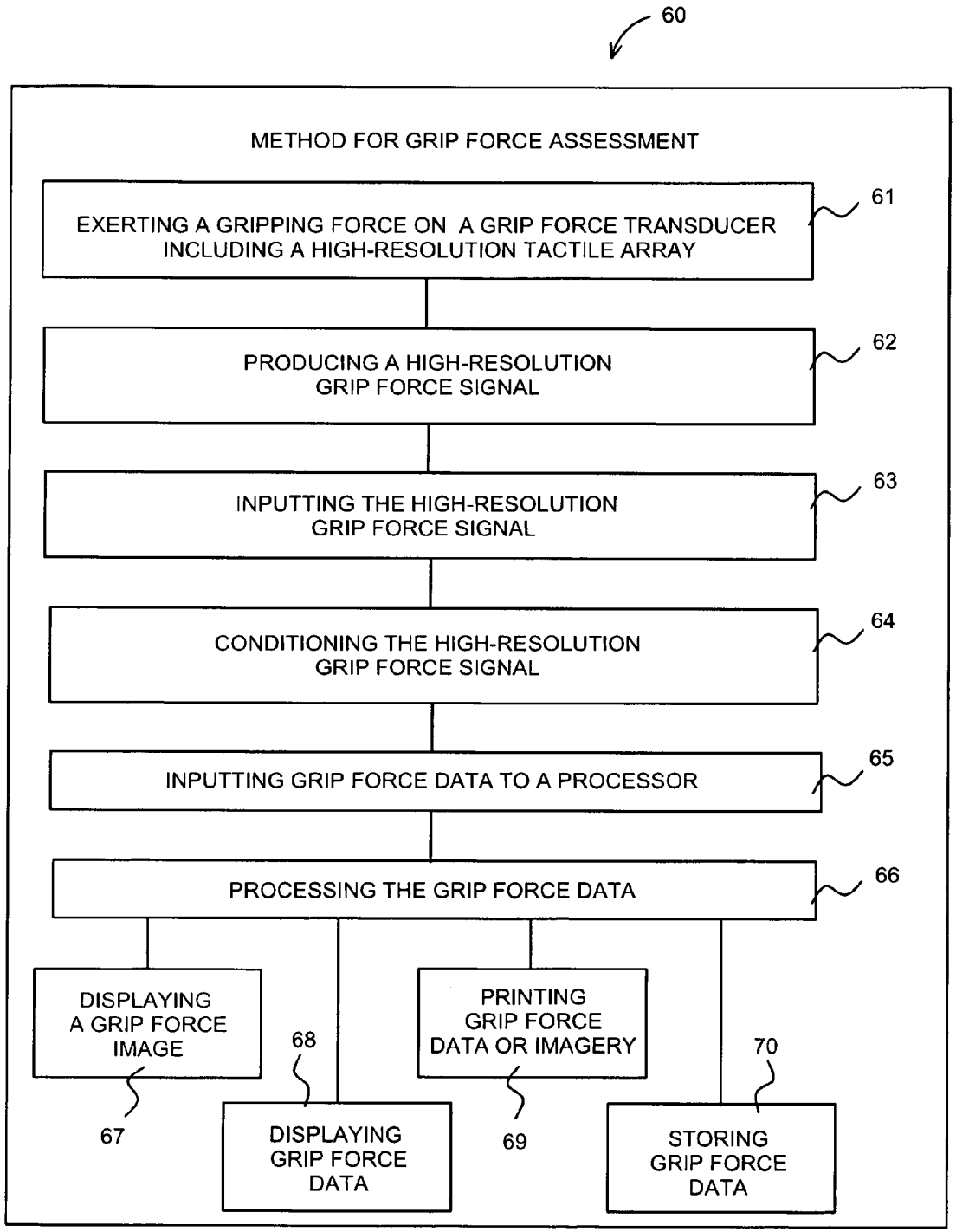
FIG. 10 is a schematic flow diagram depicting steps of a method for grip force assessment system according to the present invention.

Referring to FIG. 10 steps of a METHOD FOR GRIP FORCE ASSESSMENT 60, are discussed in greater detail. METHOD FOR GRIP FORCE ASSESSMENT 60 includes the steps of: EXERTING A GRIPPING FORCE ON A GRIP FORCE TRANSDUCER INCLUDING A HIGH-RESOLUTION TACTILE ARRAY 61, PRODUCING A HIGH-RESOLUTION GRIP FORCE SIGNAL 62, INPUTTING THE HIGH-RESOLUTION GRIP FORCE SIGNAL 63, CONDITIONING THE HIGH-RESOLUTION GRIP FORCE SIGNAL 64, INPUTTING GRIP FORCE DATA TO A PROCESSOR 65 and PROCESSING THE GRIP FORCE DATA 66. The METHOD FOR GRIP FORCE ASSESSMENT 60 may also include the steps of DISPLAYING A GRIP FORCE IMAGE 67, DISPLAYING GRIP FORCE DATA 68, PRINTING A GRIP FORCE DATA OR IMAGERY 69 and/or STORING GRIP FORCE DATA 70.

Referring to FIGS. 1 and 9, at EXERTING A GRIPPING FORCE ON A GRIP FORCE TRANSDUCER INCLUDING A HIGH-RESOLUTION TACTILE ARRAY 61 a subject grasps grip force transducer 10, (shown in FIG. 1), that includes a high-resolution tactile array and exerts a gripping force over a period of time, typically as specified by one conducting an assessment. Exerting a gripping force on a grip force transducer that includes a high-resolution tactile array results in the step of PRODUCING A HIGH-RESOLUTION GRIP FORCE SIGNAL 62. Referring to FIG. 3, the high-resolution grip force signal generated by the grip force transducer 10 including a high-resolution tactile array 20 comprises signals from each of the plurality of nodes 21 that vary over the course of time as the grip force varies.

At INPUTTING THE HIGH-RESOLUTION GRIP FORCE SIGNAL 63, the high-resolution grip force signal is input to signal conditioning module 25, shown in FIG. 1. At CONDITIONING THE HIGH-RESOLUTION GRIP FORCE SIGNAL 64, amplification, modulation, multiplexing and digitizing the high-resolution grip force signal is performed. Conditioned grip force data from CONDITIONING THE HIGH-RESOLUTION GRIP FORCE SIGNAL 64, and referring to FIG. 1, is input to processing device 30 at INPUTTING GRIP FORCE DATA TO A PROCESSOR 65. At PROCESSING THE GRIP FORCE DATA 66, processing device 30 executes a variety of processes including analytical and graphical functions. Referring to FIG. 1, analytical functions are performed by processor 30 employing grip force analytical software 33 that provides interpolation of data derived from the plurality of nodes. Additionally, grip force analytical software 33 may tabulate various force values including maximum, average and total forces as well as calculate contact area of the effective grip.

At DISPLAYING A GRIP FORCE IMAGE 67, referring to FIG. 8, a user may display and interface with grip force screen display 42, or the various parts thereof including grip force map image 45. Data may be displayed across a wide range of force displays from zero to approximately 14 kilograms/cm², (1378960 newtons/m²), or (200 psi). Grip force assessment system 50 provides the user with an ability to view and assess grip force in real time providing imagery depicting the function of individual fingers, and the complex grip capability/capacity of the entire hand. Grip force assessment system 50 also provides the user with an ability to manipulate grip force map image 45, shown in FIG. 8, by magnification, rotation, variation of image resolution, variation of force scales and variation of image color spectrum. One advantage to employing high-resolution tactile array 20, shown in FIG. 3, is found in the resulting display as the closer the individual nodes 21 are to one another the more accurate interpolation of grip force between nodes becomes and hence the more accurate and informative the representation and imagery of the grip force data becomes.

At DISPLAYING GRIP FORCE DATA 68, a user has the option of viewing At PRINTING GRIP FORCE DATA OR IMAGERY 69, the processing device may, referring to FIG. 1, command imaging device 44 to produce an image of grip force screen display 42, (shown in FIG. 8), or the various parts thereof including grip force map image 45. Alternately, a user may elect to print grip force data in table or other textual format. Additionally, the user may elect at STORING GRIP FORCE DATA 70 to store grip force data for later review, analysis and assessment.

The foregoing description of the illustrated embodiments has been presented for purposes of illustration and description. It is not intended to be exhaustive or to limit the invention to the precise form or to exemplary embodiment(s) and implementation(s) disclosed. Numerous modifications and variations will be apparent to practitioners skilled in this art. Process steps described might be interchangeable with other steps in order to achieve the same result. At least one preferred embodiment was chosen and described in order to best explain the principles of the invention and a best mode of practical application, thereby to enable others skilled in the art to understand the invention for various embodiments and with various modifications as are suited to the particular use or implementation contemplated. It is intended that the scope of the invention be defined by the claims appended hereto and their equivalents. Reference to an element in the singular is not intended to mean "one and only one" unless explicitly so stated, but rather means "one or more." Moreover, no element, component, or method step in the present disclosure is intended to be dedicated to the public regardless of whether the element, component, or method step is explicitly recited in the following claims. No claim element herein is to be construed under the provisions of 35 U.S.C. Sec. 112, sixth paragraph unless the element is expressly recited using the phrase "means for . . . ".

What is claimed is:

1. A method for grip force assessment employing a grip force assessment system including the steps of:
    exerting a gripping force on a grip force transducer including a high-resolution tactile array generating a high-resolution grip force signal;
    inputting the high-resolution grip force signal to the signal conditioning module;
    conditioning the high-resolution grip force signal producing grip force data;
    inputting grip force data to a processor; and
    processing the grip force data, performing a numerical analysis of said grip force data; and
    outputting grip force data representative of individual finger function relative to entire hand function.

2. The method for grip force assessment of claim 1 wherein the step of conditioning the high-resolution grip force signal includes an additional step selected from the list of steps including amplification of the high-resolution grip force signal, modulation of the high-resolution grip force signal, multiplexing of the high-resolution grip force signal and digitizing the high-resolution grip force signal.

3. The method for grip force assessment of claim 1 wherein the step of processing the grip force data includes performing a statistical analysis of the grip force data.

4. The method for grip force assessment of claim 1 wherein the step of processing the grip force data includes generating a grip force map image representative of contact force distribution of individual finger function relative to entire hand function.

5. The method for grip force assessment of claim 1 wherein the step of displaying the grip force data includes:
    generating a grip force map image representative of contact force distribution of individual finger function relative to entire hand function; and
    manipulating the grip force map image.

6. The method for grip force assessment of claim 1 wherein the step of processing the grip force data includes generating a real time grip force map image representative of contact force distribution of individual finger function relative to entire hand function.

7. The method for grip force assessment of claim 1 also including the step of printing a grip force map image.

8. The method for grip force assessment of claim 1 also including the step of storing grip force data.

* * * * *